United States Patent [19]

Kolich

[11] Patent Number: 5,344,970
[45] Date of Patent: Sep. 6, 1994

[54] HYDROGENATION OF AROMATIC-SUBSTITUTED OLEFINS USING ORGANOMETALLIC CATALYST

[75] Inventor: Charles H. Kolich, Baton Rouge, La.

[73] Assignee: Albemarle Corporation, Richmond, Va.

[21] Appl. No.: 173,795

[22] Filed: Dec. 22, 1993

Related U.S. Application Data

[60] Continuation of Ser. No. 57,380, May 6, 1993, abandoned, which is a continuation of Ser. No. 989,433, Dec. 11, 1992, abandoned, which is a division of Ser. No. 787,101, Nov. 4, 1991, Pat. No. 5,210,243, which is a continuation-in-part of Ser. No. 624,571, Dec. 10, 1990, abandoned.

[51] Int. Cl.$^5$ .............................................. C07C 53/134
[52] U.S. Cl. .................... 562/496; 562/465; 562/466; 562/467; 562/480; 562/490; 560/56; 560/80; 560/100; 560/105; 558/6; 558/426; 564/170; 564/171; 564/182
[58] Field of Search ............... 562/496, 465, 466, 467, 562/480, 490; 560/56, 80, 100, 105; 564/170, 171, 182; 558/6, 100, 101

[56] References Cited

U.S. PATENT DOCUMENTS

| | | | |
|---|---|---|---|
| 4,152,351 | 5/1979 | Drake | 562/496 |
| 4,962,230 | 10/1990 | Takaya | 562/496 |
| 5,087,728 | 2/1992 | Nohiya et al. | 562/496 |
| 5,177,231 | 1/1993 | Manimaran | 556/21 |
| 5,187,135 | 2/1993 | Kolich et al. | 502/162 |
| 5,187,136 | 2/1993 | Kolbucar et al. | 502/162 |
| 5,187,281 | 2/1993 | Kolich et al. | 556/16 |
| 5,190,905 | 3/1993 | Kolich et al. | 502/162 |
| 5,191,095 | 3/1993 | Manimaran | 554/35 |
| 5,202,472 | 4/1993 | Manimaran | 562/493 |
| 5,202,473 | 4/1993 | Chan et al. | 562/496 |

FOREIGN PATENT DOCUMENTS

92/09552 6/1992 PCT Int'l Appl.

Primary Examiner—Paul J. Killos
Attorney, Agent, or Firm—Richard J. Hammond

[57] ABSTRACT

A ruthenium-phosphite complex having the formula

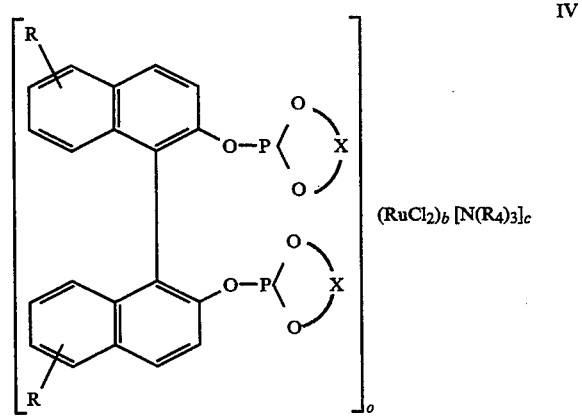

IV wherein a is from 1 to 3; b is 1 or 2; c is from 0 to 3; and R is hydrogen, alkyl, aryl, halo, amino, acetylamino, or sulfo; and X is

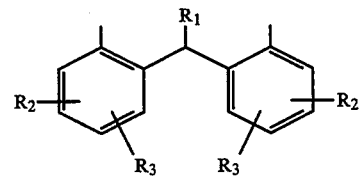

where $R_1$, $R_2$, and $R_3$ are the same or different and are hydrogen or $C_1$ to $C_6$ linear or branched alkyl.

This complex can be used to effect the reduction of unsaturated organic compounds or, when comprised of ligands having optical activity, can be used as the catalyst for effecting the asymmetric reduction of unsaturated organic compounds.

4 Claims, No Drawings

HYDROGENATION OF AROMATIC-SUBSTITUTED OLEFINS USING ORGANOMETALLIC CATALYST

This application is a continuation of application Ser. No. 08/057,380, filed May 6, 1993, abandoned, which is a continuation of 07/989,433, filed Dec. 11, 1992, abandoned, which is a division of application Ser. No. 07/787,101, filed Nov. 4, 1991, now U.S. Pat. No. 5,210,243 which is a continuation-in-part of 07/624,571, filed Dec. 10, 1990, abandoned.

FIELD OF THE INVENTION

This invention relates to a process for the catalytic reduction of aromatic-substituted olefins. More specifically, this invention relates to a process for asymmetrically, catalytically reducing aromatic-substituted olefins using organoruthenium phosphites.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, an appropriate element of symmetry, substituents capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., Tetrahedron, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; and 4,766,227. Unlike the more classical models of chiral (asymmetric) molecules, chirality in the case of the BINAP compounds arises from the restricted rotation about the single bond joining the naphthalene rings. Because of such restricted rotation, perpendicular disymmetric planes result. Isomers arising from this type of asymmetry are termed atropisomers.

Cationic rhodium-BINAP complex has been shown to catalyze the isomerization of allylamines to chiral enamines in 94–96% ee. Also, hydrogenations of geraniol and nerol (bis-unsaturated alcohols) using rhodium-BINAP complexes produce products in about 50% ee's. The synthesis of BINAP derivatives bearing groups other than phenyl on phosphorus such as paramethylphenyl and cyclohexyl have also been prepared. Inoue, et al., Chem. Lett., 1985, 1007.

The BINAP ruthenium complexes have been used to catalyze a variety of asymmetric hydrogenations including the hydrogenation of enamides, alkyl and aryl-substituted acrylic acids, homoalkylic alcohols and functionalized ketones. See Noyori, et al., Modern Synthetic Methods, 1989, 5, 115, incorporated herein by reference. While these complexes are effective in facilitating the asymmetric reduction of these compounds, they are difficult to prepare and expensive to produce.

SUMMARY OF THE INVENTION

The present invention involves a novel organoruthenium-phosphite catalyst which can be used to effect the reduction of unsaturated organic compounds or, when comprised of ligands having optical activity, can be used as the catalyst for effecting the asymmetric reduction of unsaturated organic compounds.

The catalyst referred to herein is represented by the formula

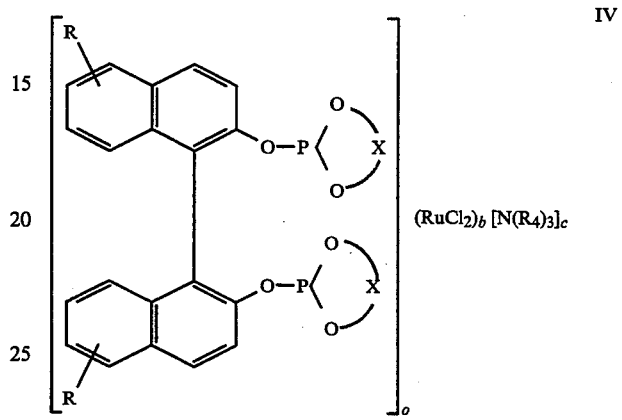

where a is from 1 to 3; b is 1 or 2; c is from 0 to 3; and R is hydrogen, alkyl, aryl, halo, amino, acetylamino, or sulfo and X is

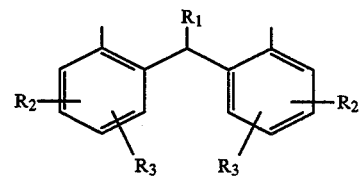

where $R_1$, $R_2$, and $R_3$ are the same or different and are hydrogen or $C_1$ to $C_6$ linear or branched alkyl; and $R_4$, taken together with the nitrogen atom, is a tertiary amine that is aliphatic, aromatic or mixed aliphatic-/aromatic tertiary amine. Thus, $R_4$ can be the following:

Straight or branched chain alkyl having 1 to 20 carbon atoms which includes, for example, methyl, ethyl, propyl, isopropyl, butyl, isobutyl, secondary butyl, tertiary butyl, pentyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

Cycloalkyl having 3 to 7 carbon atoms and includes cyclopropyl, cyclobutyl, cyclopentyl, cyclohexyl and cycloheptyl;

Phenyl; phenyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

Heteroaryl, i.e., 5 to 10 membered mono- of fused-heteroaromatic ring which as at least one heteroatom selected from the group consisting of nitrogen, oxygen, and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl;

Substituted heteroaryl, i.e., 5 to 10 membered mono- of fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus and includes, for example, 1-pyrrolidinyl, 2-oxo-1-pyrrolidinyl, piperidino, 1-piperazinyl, 4-methyl-1-piperazinyl, 4-(2-hydroxyethyl)-1-piperazynyl, 4-benzylpiperazinyl, 1-homopiperazynyl, morpholino and thiomorpholino;

Haloalkyl, i.e., straight or branched chain alkyl having 1 to 10 carbon atoms which is substituted with at least one halogen as mentioned above; or Alkoxyalkyl, i.e., that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, oxtyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexylocyoctyl and 8-octyloxyoctyl.

DETAILED DESCRIPTION OF THE PREFERRED EMBODIMENTS

The novel organo ruthenium phosphite complex according to the present invention can be prepared by first reacting the readily available phosphonite

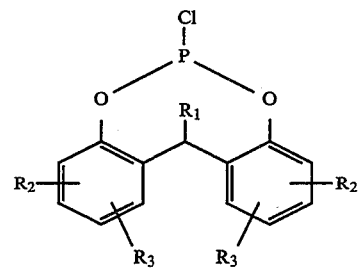

where $R_1$, $R_2$, and $R_3$ are the same or different and are hydrogen or $C_1$ to $C_6$ linear or branched alkyl with the chiral diol

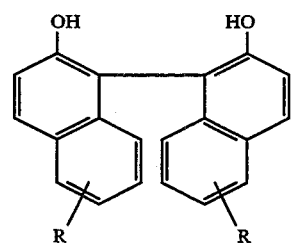

where R is hydrogen, alkyl, aryl, halo, amino, acetylamino, or sulfo to produce the phosphite intermediate

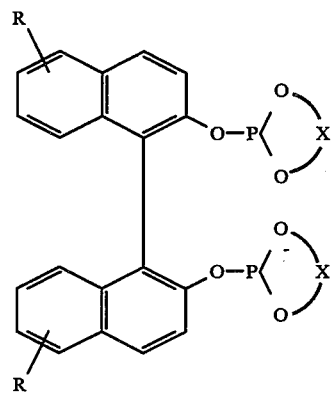

where R is as defined above and X is the group

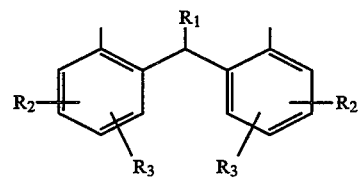

where $R_1$, $R_2$, and $R_3$ are defined above.

The reaction of compounds I and II proceeds easily, typically at room temperature using an inert polar organic solvent (tetrahydrofuran is particularly preferred) in the presence of an acid scavenger (triethylamine is particularly preferred). Reactions of this type are well known in the prior art.

The phosphite intermediate III is converted to the organo ruthenium phosphite by reacting [Ru(COD)Cl$_2$]$_n$ polymer, where COD represents 1,5-cyclooctadiene, with one or more equivalents of compound III in the presence of about four equivalents of tertiary amine in an inert solvent, typically at elevated temperature.

It should be noted, however, that other stoichiometries will produce ruthenium complexes of the same general formula shown for IV that are also active hydrogenation catalysts.

Examples of tertiary amines which can be used in the present invention include triethylamine, tri-n-butylamine, tri-n-hexylamine, N-methylpiperidine, pyridine, dimethylaniline, etc.

$[RuCl_2(COD)]_n$ which is used in the present invention can be obtained by reacting ruthenium chloride with cycloocta-1,5-diene in an ethanol solution as disclosed in, for example, M. A. Bennett, et al., Chemistry and Industry (1959) 1516.

The reactants of Formula I employed as precursors for the preparation of the complexes of the present invention are prepared by reacting the appropriate bridged phenolic compound with phosphorous trichloride. The reaction is typically conducted in an aprotic solvent such as tetrahydrofuran or benzene. However, the reaction can also be carried out in an excess of phosphorous trichloride which functions as a solvent and as a reactant. Temperatures are typically adjusted so that the reaction proceeds at a reasonable rate, i.e., $-30°$ C. to $300°$ C. The preparation of these precursor compounds is described in detail in U.S. Pat. No. 4,912,155 and in U.S. patent application Ser. No. 487,880 filed Mar. 5, 1990, both incorporated herein by reference.

The above catalysts are useful in stereoselective hydrogenation of olefinic compounds of the formula

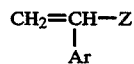

where Z is $-C(O)OR'$, where $R'$ is hydrogen or $C_1$ to $C_6$ linear or branched alkyl, $-CN$, $-C(NH)OR''$, where $R''$ is $C_1$ to $C_6$ linear or branched alkyl, or $-C(O)NH_2$; and Ar is phenyl or naphthyl unsubstituted or substituted with $C_1$ to $C_6$ linear or branched alkyl, $C_1$ to $C_6$ linear or branched alkoxy, halo (fluoro, chloro, bromo, or iodo), or carboxylic acid or $C_1$ to $C_6$ linear or branched alkyl ester thereof. Solutions of these olefins are typically admixed with a catalytically effective amount of the ruthenium compounds of the present invention and hydrogenated at about $20°$ C. to about $100°$ C. under about 20 to about 1000 psi of hydrogen.

EXAMPLES

The present invention is described in greater detail by reference to the following non limiting Examples.

EXAMPLE 1

Preparation of the Diphosphite of (S)-(−)-1,1′-Bi-2-naphthol and Compound I where $R_2=R_3=$t-butyl and $R_1$ is methyl A 0.881 g (1.75mmol) portion of 2,2′-ethylidinebis(4,6-di-t-butylphenyl) chlorophosphite (I) (mp 195°–229° C.) was combined with 0.249 g (0.87 mmol) of (S)-(−)-1,1′-bi-2-naphthol and 15.205 g of dry tetrahydrofuran in a 50-ml single-necked flask in a nitrogen-filled glove box. The clear colorless solution was then treated with 0.697 g (6.89 mmol) of dry triethylamine. After stirring the mixture for 24 hr at room temperature, the mixture was filtered in the glove box through a 0.45-micron syringe filter to remove the white triethylamine hydrochloride by-product. The clear colorless filtrate was evaporated to dryness under vacuum (0.2 torr/40° C.) to obtain 1.205 g of white crystalline diphosphite (B) having a melting range of 114°–170° C.

EXAMPLE 2

Preparation of the Ruthenium (II) Complex of B

A 0.373 g (0.306 mmol) portion of B was combined with 0.074 g (0.26/n mmol) of $[Ru(COD)Cl_2]_n$ polymer (where COD=1,5-cyclooctadiene), 15.025 g of dry toluene, and 0.107 g (1.06 mmol) of dry triethylamine in a 50-ml single-necked flask in a nitrogen-filled glove box. After refluxing for 5 hr, the cloudy brown mixture was suction filtered through a sintered glass funnel in the glove box. The light brown solid on the filter weight only 0.012 g and melted at 195°–225° C. The clear brown filtrate was evaporated to dryness under vacuum (0.2 torr/40° C.) to obtain 0.426 g of brown solid C (mp 105°–147° C.).

EXAMPLE 3

Preparation of the Diphosphite of (R)-(+)-1,1′-Bi-2-naphthol and Compound I where $R_2=R_3=$t-butyl and $R_1=$methyl This reaction was carried out as described above for the S enantiomer of binaphthol. The white crystalline diphosphite product (D) had a melting range of 100°–160° C.

EXAMPLE 4

Preparation of the Ruthenium (II) Complex of D

A 0.073 g (0.26/n mmol) portion of $[Ru(COD)Cl_2]_n$ polymer was added to a 50-ml single-necked flask containing 0.372 g (0.305 mmol) of the diphosphite D in the glove box. A 15.106 g portion of dry toluene and 0.110 g (1.09 mmol) of dry triethylamine were also added to the flask. After refluxing for 17 hr, the dark brown mixture was filtered in the glove box through a 0.45-micron syringe filter to remove a small amount of dark solid. A 15.216 g portion of n-heptane was added to the clear dark brown filtrate without causing precipitation of any solid. The solution was evaporated to dryness under vacuum (0.2 torr/70° C.) to obtain 0.471 g of dark brown catalyst E (mp 94°–114° C.).

EXAMPLE 5

Hydrogenation of 2-(4-isobutylphenyl)acrylic Acid

The catalyst was combined with 2-(4-isobutylphenyl)acrylic acid (UA) and 15 ml of nitrogen-purged solvent in a 25-ml flask in a glove box under nitrogen. This solution was transferred by syringe into a metal reactor (50-ml or 100-ml) with an additional 15 ml of solvent used to complete the transfer. The reactor was purged with hydrogen (3×1000 psi $H_2$) and then stirred at 300 rpm and 1000 psi $H_2$ under the conditions given in the following table. The % conversion of UA to ibuprofen and the enantiomeric excess (ee) as determined by HPLC analyses are also given in the table.

TABLE I

| CATALYST FROM EXAMPLES(mg) | AMOUNT UA(mg) | SOLVENT | HYDROGENATION CONDITIONS | | | (optical form) %ee |
|---|---|---|---|---|---|---|
| | | | TEMP(°C.) | TIME(hr) | CONVERSION | |
| E(19) | 239 | Methanol(a) | 24 | 88 | 69% | 20(R) |
| C(30) | 206 | Methanol | 25 | 21 | 100% | 34(S) |
| C(32) | 236 | Methanol | −5 | 64 | 67% | 7(S) |
| C(32) | 222 | Acetic acid | 24 | 20 | 8% | Not Determined |
| | | | 101 | 23 | 100% | 29(S) |
| C(32) | 208 | Cyclohexane(b) | 24 | 17 | 8% | Not Determined |
| | | | 100 | 4 | 100% | 21(S) |
| Q(33) | 202 | Cyclohexane | 24 | 21 | 0% | Not Determined |
| | | | 100 | 6 | 100% | 25(S) |
| C(28) | 206 | Methanol | 102 | 4 | 100% | 32(S) |

(a) A 130 mg portion of triethylamine was added.
(b) A trace of acetic acid was present from a previous run.
UA is 2 (4-isobutylphenyl)acrylic acid.

I claim:

1. A process for the enantioselective hydrogenation of an aromatic-substituted olefin of the formula

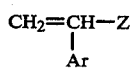

where Z is

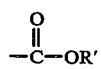

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula

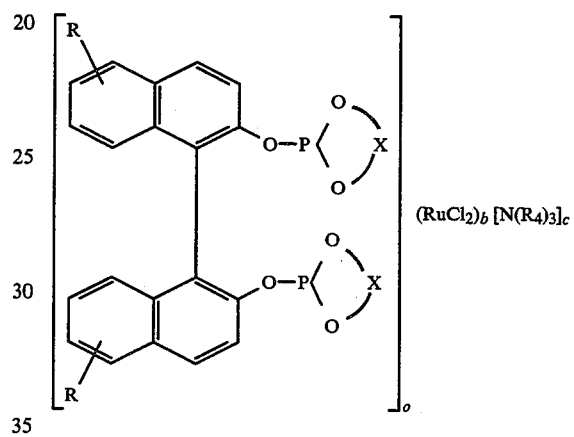

wherein a is from 1 to 3, b is 1 or 2, c is from 0 to 3; R is hydrogen, alkyl, aryl, halo, amino, acetylamino, or sulfo; and X is

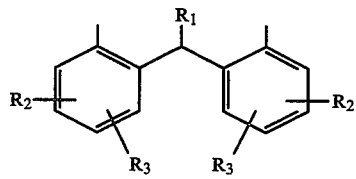

where $R_1$, $R_2$ and $R_3$ are the same or different and are hydrogen or $C_1$ to $C_6$ linear or branched alkyl; and $R_4$ taken together with the nitrogen atom is a straight or branched chain alkyl of 1 to 20 carbon atoms; in the presence of gaseous hydrogen for a time and at a temperature sufficient to effect enantiomonic reduction of at least a portion of the double bond of said olefin.

2. The process according to claim 1 where $R_1$ is methyl or ethyl.

3. The process according to claim 1 where $R_2$ and $R_3$ are the same and are isopropyl or tertiary butyl.

4. The process according to claim 1 where R is hydrogen.